(12) United States Patent
Reid et al.

(10) Patent No.: US 12,291,726 B2
(45) Date of Patent: May 6, 2025

(54) A549 HOST CELLS COMPRISING A RECOMBINANT ONCOLYTIC ADENOVIRUS WITH MODIFIED E1A CANCER-SPECIFIC PROMOTER

(71) Applicant: EpicentRx, Inc., La Jolla, CA (US)

(72) Inventors: Tony R. Reid, San Diego, CA (US); Bryan T. Oronsky, Los Altos Hills, CA (US); Christopher Larson, San Diego, CA (US)

(73) Assignee: EPICENTRX, INC., La Jolla, CA (US)

( * ) Notice: Subject to any disclaimer, the term of this patent is extended or adjusted under 35 U.S.C. 154(b) by 0 days.

(21) Appl. No.: 18/649,467

(22) Filed: Apr. 29, 2024

(65) Prior Publication Data
US 2024/0294883 A1  Sep. 5, 2024

Related U.S. Application Data

(63) Continuation of application No. 16/604,194, filed as application No. PCT/US2018/026977 on Apr. 10, 2018, now Pat. No. 11,999,973.

(60) Provisional application No. 62/483,837, filed on Apr. 10, 2017.

(51) Int. Cl.
 *C12N 5/09* (2010.01)
 *C12N 7/00* (2006.01)

(52) U.S. Cl.
 CPC ............ *C12N 5/0693* (2013.01); *C12N 7/00* (2013.01); *C12N 2710/10321* (2013.01); *C12N 2710/10322* (2013.01); *C12N 2710/10332* (2013.01); *C12N 2710/10352* (2013.01)

(58) Field of Classification Search
 CPC ........ C12N 5/0693; C12N 7/00; C12N 15/86; C12N 2710/10321
 See application file for complete search history.

(56) References Cited

U.S. PATENT DOCUMENTS

| | | | |
|---|---|---|---|
| 6,113,913 A | 9/2000 | Brough et al. | |
| 9,073,980 B2 | 7/2015 | Reid et al. | |
| 2005/0153419 A1 | 7/2005 | Liu et al. | |
| 2019/0352669 A1 | 11/2019 | Reid et al. | |

FOREIGN PATENT DOCUMENTS

| | | |
|---|---|---|
| JP | 2007515172 A | 6/2007 |
| WO | WO-2000032754 A1 | 6/2000 |
| WO | WO-2003039459 A2 | 5/2003 |
| WO | WO-2005063910 A1 | 7/2005 |
| WO | WO-2010101921 A2 | 9/2010 |

OTHER PUBLICATIONS

Gilbert, R., et al., 2014, Establishment and validation of new complementing cells for production of E1-deleted adenovirus vectors in serum-free suspension culture, J. Virol. Methods 208:177-188.*

(Continued)

*Primary Examiner* — Jeffrey S Parkin
(74) *Attorney, Agent, or Firm* — Morrison & Foerster LLP

(57) ABSTRACT

The present disclosure relates to compositions and methods for producing a recombinant virus, e.g., a recombinant oncolytic adenovirus, using an A549 host cell.

19 Claims, 3 Drawing Sheets

Specification includes a Sequence Listing.

(56) References Cited

OTHER PUBLICATIONS

Longley, Jr., R., et al., 2005, Development of a serum-free suspension process for the production of a conditionally replicating adenovirus using A549 cells, Cytotechnol. 49:161-171.*

Belluti et al., (2020). "Transcription factors in cancer: When alternative splicing determines opposite cell fates," Cells, 9(760):9030760, 28 pages.

Feng et al., (1997). "Stable in vivo gene transduction via a novel adenoviral/retroviral chimeric vector," Nature Biotechnology, 15:866-870.

Gilbert et al., (2014). "Establishment and validation of new complementing cells for production of E1-deleted adenovirus vectors in serum-free suspension culture," Journal of Virological Methods, 208:177-188.

Hedjran et al., (2011). "Deletion analysis of Ad5 E1a transcriptional control region: impact on tumor-selective expression of E1a and E1b," Cancer Gene Therapy 18:717-723.

International Search Report and Written Opinion received for International Patent Application No. PCT/US2018/026977 mailed on Jul. 16, 2018, 11 pages.

Kirn, (2000). "Replication-selective oncolytic adenoviruses: virotherapy aimed at genetic targets in cancer," Oncogene, 19(56):6660-6669.

Kirn, (2001). "Oncolytic virotherapy for cancer with the adenovirus dl1520 (Onyx-015): results of phase I and II trials," Expert Opinion On Biological Therapy, 1(3):525-538.

Kumar et al., (2008). "Virus combinations and chemotherapy for the treatment of human cancers," Current Opinion In Molecular Therapeutics, 10(4):371-379.

Longley et al., (2005). "Development of a serum-free suspension process for the production of a conditionally replicating adenovirus using A549 cells," Cytotechnology, 49:161-171.

Niemann et al., (2017). "Oncolytic viruses: adenoviruses," Virus Genes, 53:700-706.

Ramachandra et al., (2001). "Re-engineering adenovirus regulatory pathways to enhance oncolytic specificity and efficacy," Nature Biotechnology, 19:1035-1041.

Stewart, (2016). "Adenovirus structure," in Adenoviral Vectors for Gene Therapy, Elsevier, Inc., http://dx.doi.org/10.1016/B978-0-11-800276-6.00001-2, pp. 1-26.

* cited by examiner

A549 HOST CELLS COMPRISING A RECOMBINANT ONCOLYTIC ADENOVIRUS WITH MODIFIED E1A CANCER-SPECIFIC PROMOTER

CROSS-REFERENCE TO RELATED APPLICATIONS

This application is a continuation of U.S. application Ser. No. 16/604,194, which is a U.S. National Phase patent application under 35 U.S.C. § 371 of International Application No. PCT/US2018/026977, filed internationally on Apr. 10, 2018, which claims the priority benefit of U.S. Provisional Application Ser. No. 62/483,837, filed Apr. 10, 2017, the disclosures of which is are incorporated herein by reference in its their entirety.

REFERENCE TO AN ELECTRONIC SEQUENCE LISTING

The contents of the electronic sequence listing (203592001201SEQLIST.xml; Size: 47,277 bytes; and Date of Creation: Apr. 23, 2024) is herein incorporated by reference in its entirety.

TECHNICAL FIELD

The present disclosure relates to compositions and methods for producing a recombinant virus, e.g., a recombinant oncolytic adenovirus.

BACKGROUND

Despite extensive knowledge of the underlying molecular mechanisms that cause cancer, most advanced cancers remain incurable with current chemotherapy and radiation protocols. Oncolytic viruses have emerged as a platform technology that has the potential to significantly augment current standard treatment for a variety of malignancies (Kumar, S. et al. (2008) CURRENT OPINION IN MOLECULAR THERAPEUTICS 10(4):371-379; Kim, D. (2001) EXPERT OPINION ON BIOLOGICAL THERAPY 1(3):525-538; Kim D. (2000) ONCOGENE 19(56):6660-6669). These viruses have shown promise as oncolytic agents that not only directly destroy malignant cells via an infection-to-reproduction-to-lysis chain reaction but also indirectly induce anti-tumor immunity. These immune stimulatory properties have been augmented with the insertion of therapeutic transgenes that are copied and expressed each time the virus replicates.

Previously developed oncolytic viruses include the oncolytic serotype 5 adenovirus (Ad5) referred to as TAV-255 that is transcriptionally attenuated in normal cells but transcriptionally active in cancer cells (see, PCT Publication No. WO2010/101921). It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences.

Despite the efforts to date, there is a need for improved viruses for treating cancers and hyperproliferative disorders in human patients, and improved methods for producing recombinant viruses.

SUMMARY OF THE INVENTION

The invention is based, in part, upon the discovery that an A549 host cell, e.g., a SF-BMAdR 281 A549 host cell, can be used to produce large quantities of a recombinant virus, e.g., an oncolytic adenovirus. It has surprisingly has been found that certain recombinant viruses, e.g., recombinant oncolytic adenoviruses, grow to higher densities in a replication permissive environment in serum-free and suspension-adapted A549 cells than in HEK293 cells, which are widely used for viral vector production.

Accordingly, in one aspect, the invention provides a method for producing a recombinant virus comprising: (a) infecting an A549 host cell with a recombinant virus to produce an infected A549 host cell; and (b) suspension culturing the infected A549 host cell in a serum-free medium, under conditions (e.g., in a replication permissive environment) to permit replication of the recombinant virus, thereby to produce the recombinant virus. In certain embodiments, the A549 host cell is a SF-BMAdR 281 A549 host cell. In certain embodiments, the infected A549 host cell is cultured for at least 3 days.

The method may further comprise, after step (b), the step of purifying the recombinant virus. The step of purifying the recombinant virus may comprise one or more of lysing the infected A549 host cell, nuclease treatment, and ion exchange chromatography, e.g., anion exchange chromatography. In certain embodiments, the step of purifying the recombinant virus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant virus than a comparable method for producing a recombinant virus. For example, in certain embodiments, the method results in at least 5×, 10×, or 20× more recombinant virus compared to a similar method (e.g., an otherwise identical method) that comprises, in step (a), infecting a HEK293 host cell with a recombinant virus to produce an infected HEK293 host cell, and, in step (b), suspension culturing the infected HEK293 host cell in a serum-free medium, under conditions (e.g., in a replication permissive environment) to permit replication of the recombinant virus. In certain embodiments, the method results in at least 5×, 10×, or 20× more recombinant virus compared to a similar method (e.g., an otherwise identical method) that comprises, in step (b), adherent culturing the infected A549 host cell in a serum-free medium, under conditions (e.g., in a replication permissive environment) to permit replication of the recombinant virus. In certain embodiments, the method results in at least 5×, 10×, or 20× more recombinant virus compared to a similar method (e.g., an otherwise identical method) that comprises, in step (b), suspension culturing the infected A549 host cell in a serum-containing medium, under conditions (e.g., a replication permissive environment) to permit replication of the recombinant virus.

In certain embodiments, the recombinant virus is an adenovirus, e.g., a type 5 adenovirus, or an adeno-associated virus. In certain embodiments, the recombinant virus is a recombinant oncolytic virus. In certain embodiments, the recombinant virus is a recombinant oncolytic adenovirus.

In another aspect, the invention provides a method for producing a recombinant oncolytic adenovirus comprising: (a) infecting an A549 host cell with a recombinant oncolytic adenovirus to produce an infected A549 host cell; and (b) suspension culturing the infected A549 host cell in a serum-free medium, under conditions (e.g., in a replication permissive environment) to permit replication of the recombinant oncolytic adenovirus, thereby to produce the recombinant oncolytic adenovirus. In certain embodiments, the A549 host cell is a SF-BMAdR 281 A549 host cell. In certain embodiments, the infected A549 host cell is cultured for at least 3 days.

The method may further comprise, after step (b), the step of purifying the recombinant oncolytic adenovirus. The step of purifying the recombinant oncolytic adenovirus may comprise one or more of lysing the infected A549 host cell, nuclease treatment, and ion exchange chromatography, e.g., anion exchange chromatography. In certain embodiments, the step of purifying the recombinant oncolytic adenovirus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant oncolytic adenovirus than a comparable method for producing a recombinant oncolytic adenovirus. For example, in certain embodiments, the method results in at least 5×, 10×, or 20× more recombinant oncolytic adenovirus compared to a similar method (e.g., an otherwise identical method) that comprises, in step (a), infecting a HEK293 host cell with a recombinant oncolytic adenovirus to produce an infected HEK293 host cell, and, in step (b), suspension culturing the infected HEK293 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), adherent culturing the infected A549 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), suspension culturing the infected A549 host cell in a serum-containing medium, under conditions (e.g., in a replication permissive environment) to permit replication of the recombinant oncolytic adenovirus.

In another aspect, the invention provides a method for producing a recombinant oncolytic adenovirus comprising: (a) introducing a nucleic acid comprising a nucleotide sequence encoding a recombinant oncolytic adenovirus into an A549 host cell; and (b) suspension culturing the A549 host cell in a serum-free medium, under conditions (e.g., in a replication permissive environment) to permit production of the recombinant oncolytic adenovirus, thereby to produce the recombinant oncolytic adenovirus. In certain embodiments, the A549 host cell is a SF-BMAdR 281 A549 host cell. In certain embodiments, the A549 host cell is cultured for at least 3 days.

The method may further comprise, after step (b), the step of purifying the recombinant oncolytic adenovirus. The step of purifying the recombinant oncolytic adenovirus may comprise one or more of lysing the A549 host cell, nuclease treatment, and ion exchange chromatography, e.g., anion exchange chromatography. In certain embodiments, the step of purifying the recombinant oncolytic adenovirus comprises: (i) lysing the A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant oncolytic adenovirus than a comparable method for producing a recombinant oncolytic adenovirus. For example, in certain embodiments, the method results in at least 5×, 10×, or 20× more recombinant oncolytic adenovirus compared to a similar method (e.g., an otherwise identical method) that comprises, in step (a), introducing a nucleic acid comprising a nucleotide sequence encoding a recombinant oncolytic adenovirus into a HEK293 host cell, and, in step (b), suspension culturing the HEK293 host cell in a serum-free medium, under conditions (e.g., in a replication permissive environment) to permit production of the recombinant oncolytic adenovirus. In certain embodiments, the method results in at least 5×, 10×, or 20× more recombinant oncolytic adenovirus compared to a similar method (e.g., an otherwise identical method) that comprises, in step (b), adherent culturing the A549 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), suspension culturing the A549 host cell in a serum-containing medium, under conditions (e.g., in a replication permissive environment) to permit replication of the recombinant oncolytic adenovirus.

In certain embodiments, the recombinant oncolytic adenovirus comprises an E1a promoter having a deletion of a functional Pea3 binding site. For example, the virus may comprise a deletion of nucleotides corresponding to about-300 to about-250 upstream of the initiation site of E1a, e.g., a deletion of nucleotides corresponding to −305 to −255 or −304 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 2).

In certain embodiments, the recombinant oncolytic adenovirus comprises an E1a promoter having a deletion of a functional TATA box, e.g., the deletion of an entire TATA box. For example, in certain embodiments, the virus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a polynucleotide deletion that results in a virus comprising the sequence CTAGGACTG (SEQ ID NO: 3), AGTGCCCG (SEQ ID NO: 8), or TATTCCCG (SEQ ID NO: 9), which result from joining the two polynucleotide sequences that would otherwise flank the deleted polynucleotide sequence.

In certain embodiments, the recombinant oncolytic adenovirus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 3), which results from joining the two polynucleotide sequences that would otherwise flank the deleted polynucleotide sequence.

In certain embodiments, the recombinant oncolytic adenovirus comprises an E1a promoter having a deletion of a functional CAAT box, e.g., the deletion of an entire CAAT box. For example, in certain embodiments, the virus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 10), which results from joining the two polynucleotide sequences that would otherwise flank the deleted polynucleotide sequence.

In certain embodiments, the recombinant oncolytic adenovirus comprises a nucleotide sequence encoding a transgene, which may, e.g., be inserted into an E1b-19K insertion site, wherein the E1b-19K insertion site is located between the start site of E1b-19K and the start site of E1b-55K. In certain embodiments, the E1b-19K insertion site is located between the start site of E1b-19K and the stop site of E1b-19K. In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, the nucleotide sequence encoding the transgene is inserted between nucleotides corresponding to 1714 and 1917 or between nucleotides corresponding to 1714 and 1916 of the Ad5 genome (SEQ ID NO: 1). In certain embodiments, the nucleotide sequence encoding the transgene is inserted between CTGACCTC (SEQ ID NO: 4) and TCACCAGG (SEQ ID NO: 5), e.g., the virus comprises, in a 5' to 3' orientation, CTGACCTC (SEQ ID NO: 4), the nucleotide sequence encoding the transgene, and TCACCAGG (SEQ ID NO: 5).

In certain embodiments, the nucleotide sequence encoding the transgene is not operably linked to an exogenous promoter sequence.

In certain embodiments, the transgene encodes a polypeptide selected from CD80, CD137L, IL-23, IL-23A/p19, p40, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

In certain embodiments, the recombinant virus, e.g., the recombinant oncolytic adenovirus, may selectively replicate in a hyperproliferative cell and/or selectively express the transgene in a hyperproliferative cell. The hyperproliferative cell may be a cancer cell.

In another aspect, the invention provides a recombinant virus, e.g., a recombinant oncolytic adenovirus, produced by a method disclosed herein.

In another aspect, the invention provides a method of treating cancer in a subject in need thereof, the method comprising administering to the subject an effective amount of a recombinant virus, e.g., a recombinant oncolytic adenovirus, produced by a method disclosed herein to treat the cancer in the subject.

These and other aspects and advantages of the invention are illustrated by the following figures, detailed description and claims.

DESCRIPTION OF THE DRAWINGS

The invention can be more completely understood with reference to the following drawings.

DETAILED DESCRIPTION

Figure 1:
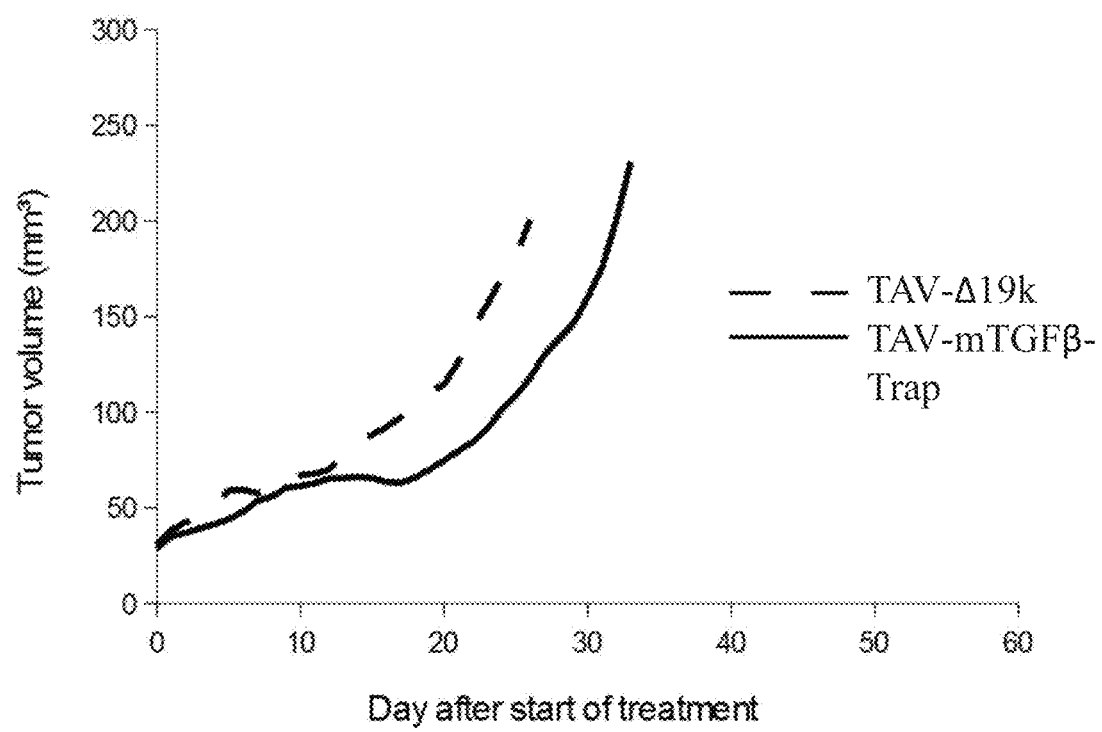
FIG. 1 is a line graph depicting mean tumor volumes in mice following treatment with the indicated virus.

The invention is based, in part, upon the discovery that an A549 host cell, e.g., a SF-BMAdR 281 A549 host cell, can be used to produce large quantities of a recombinant virus, e.g., an oncolytic adenovirus. It has surprisingly has been found that certain recombinant viruses, e.g., recombinant oncolytic adenoviruses, grow to higher densities in a replication permissive environment in serum-free and suspension-adapted A549 cells than in HEK293 cells, which are widely used for viral vector production.

Accordingly, in one aspect, the invention provides a method for producing a recombinant virus comprising: (a) infecting an A549 host cell with a recombinant virus to produce an infected A549 host cell; and (b) suspension culturing the infected A549 host cell in a serum-free medium, under conditions (e.g., in a replication permissive environment) to permit replication of the recombinant virus, thereby to produce the recombinant virus. In certain embodiments, the recombinant virus is an adenovirus, e.g., a type 5 adenovirus, or an adeno-associated virus. In certain embodiments, the recombinant virus is a recombinant oncolytic virus. In certain embodiments, the recombinant virus is a recombinant oncolytic adenovirus.

In another aspect, the invention provides a method for producing a recombinant oncolytic adenovirus comprising: (a) infecting an A549 host cell with a recombinant oncolytic adenovirus to produce an infected A549 host cell, and (b) suspension culturing the infected A549 host cell in a serum-free medium, under conditions (e.g., in a replication permissive environment) to permit replication of the recombinant oncolytic adenovirus, thereby to produce the recombinant oncolytic adenovirus.

In another aspect, the invention provides a method for producing a recombinant oncolytic adenovirus comprising: (a) introducing a nucleic acid comprising a nucleotide sequence encoding a recombinant oncolytic adenovirus into an A549 host cell, and (b) suspension culturing the A549 host cell in a serum-free medium, under conditions (e.g., in a replication permissive environment) to permit production of the recombinant oncolytic adenovirus, thereby to produce the recombinant oncolytic adenovirus. The nucleic acid can be introduced into the cell using any method known in the art, e.g., liposome-based transfection, chemical-based transfection (e.g., utilizing calcium phosphate, cationic polymers, DEAE-5 dextran, or activated dendrimers), microinjection, electroporation, nanoparticles, or cell squeezing. The nucleic acid may, for example, be part of a plasmid, or may, for example, be part of more than one plasmid.

In certain embodiments of any of the foregoing methods, the A549 host cell is a SF-BMAdR 281 A549 host cell.

An A549 host cell, e.g., an infected A549 host cell, may be cultured for at least 1 day, at least 2 days, at least 3 days, at least 4 days, at least 5 days, at least 6 days, or at least 7 days.

Following production, viral particles are recovered from the culture and optionally purified. Typical purification steps may include centrifugation, e.g., cesium chloride gradient centrifugation, clarification, enzymatic treatment, e.g., nuclease or protease treatment, chromatographic steps, e.g., ion exchange chromatography, (e.g., anion exchange chromatography), or filtration steps. Accordingly, in certain embodiments, any of the foregoing methods further comprise, after step (b), the step of purifying a recombinant virus, e.g., a recombinant oncolytic adenovirus. The step of purifying the recombinant virus, e.g., the recombinant oncolytic adenovirus, may comprise lysing an A549 host cell, e.g., an infected A549 host cell, nuclease treatment, and/or ion exchange chromatography, e.g., anion exchange chromatography. In certain embodiments, the step of purifying the recombinant virus, e.g., the recombinant oncolytic adenovirus, comprises: (i) lysing an A549 host cell, e.g., an infected A549 host cell, to produce a cell lysate; (ii) treating the cell lysate with nuclease to produce a treated cell lysate; and (iii) purifying the recombinant virus from the treated cell lysate by ion exchange chromatography, e.g., anion exchange chromatography.

In certain embodiments, any of the foregoing methods may result in a greater yield of recombinant virus, e.g., recombinant oncolytic adenovirus, than a comparable method for producing a recombinant virus. For example, in certain embodiments, a method may result in greater yield of recombinant virus, e.g., recombinant oncolytic adenovirus, compared to a similar method that is the same method but for the use of a different host cell type. Viral yield can be assayed by any method known in the art, including, e.g., qPCR, immunocytochemistry, or a luciferase reporter assay.

For example, in certain embodiments, a method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (a), infecting a HEK293 host cell with a recombinant virus to produce an infected HEK293 host cell, and, in step (b), suspension culturing the infected HEK293 host cell in a serum-free medium, under conditions (e.g., in a replication permissive environment) to permit replication of the recombinant virus. In certain embodiments, a method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (a), introducing a nucleic acid comprising a nucleotide sequence encoding a recombinant oncolytic adenovirus into a HEK293 host cell, and, in step (b), suspension culturing the HEK293 host cell in a serum-free medium, under conditions (e.g., in a replication permissive environment) to permit replication of the recombinant virus.

In certain embodiments, the method may result in greater yield of recombinant virus, e.g., recombinant oncolytic adenovirus, compared to a similar method that is the same method but for the use of adherent culture in place of suspension culture. For example, in certain embodiments, the method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (b), adherent culturing an A549 host cell, e.g., an infected A549 host cell, in a serum-free medium, under conditions (e.g., in a replication permissive environment) to permit replication of the recombinant virus. In certain embodiments, the method may result in greater yield of recombinant virus, e.g., recombinant oncolytic adenovirus, compared to a similar method that is the same method but for the use of serum-containing media in place of serum-free media. For example, in certain embodiments, the method results in at least 2×, at least 3×, at least 4×, at least 5×, at least 10×, at least 15×, at least 20×, at least 25×, or at least 30× more recombinant virus e.g., recombinant oncolytic adenovirus, compared to a similar method (e.g., an otherwise identical method) that comprises, in step (b), suspension culturing an A549 host cell, e.g., an infected A549 host cell, in a serum-containing medium, under conditions (e.g., in a replication permissive environment) to permit replication of the recombinant virus.

In certain embodiments, a method further comprises contacting an A549 host cell with an epigenetic agent, e.g., a DNMT, HDAC, and/or tyrosine kinase inhibitor, Exemplary epigenetic agents include vorinostat, romidepsin, azacitidine, decitabine, RRx-001 and CUDC-101. In certain embodiments, a method further comprises contacting an A549 host cell with an interferon. In certain embodiments, a method further comprises contacting an A549 host cell with an antioxidant, e.g., vitamin C, vitamin E, glutathione, or N-acetylcysteine.

Various features and aspects of the invention are discussed in more detail below.

I. Viruses

The term "virus" is used herein to refer any of the obligate intracellular parasites having no protein-synthesizing or energy-generating mechanism. The viral genome may be RNA or DNA. A recombinantly modified virus is referred to herein as a "recombinant virus." A recombinant virus may, e.g., be modified by recombinant DNA techniques to be replication deficient, conditionally replicating, or replication competent, and/or be modified by recombinant DNA techniques to include expression of exogenous transgenes. Chimeric viral vectors which exploit advantageous elements of each of the parent vector properties (Sec, e.g., Feng et al. (1997) NATURE BIOTECHNOLOGY 15:866-870) may also be useful in the practice of the present invention. Although it is generally favored to employ a virus from the species to be treated, in some instances it may be advantageous to use vectors derived from different species that possess favorable pathogenic features.

In certain embodiments, the recombinant virus is an oncolytic virus, e.g., a virus that exhibits tumor-selective replication and/or viral mediated lysis. In certain embodiments, the oncolytic virus allows for selective expression of a gene, e.g., a transgene. For example, in certain embodiments, the virus permits expression of the gene in neoplastic cells, but attenuates expression in normal cells. In certain embodiments, the expression of the gene in a non-hyperproliferative cell is about 90%, about 80%, about 70%, about 60%, about 50%, about 40%, about 30%, about 20%, about 10%, or about 5% of the expression of in a hyperproliferative cell. In certain embodiments, the virus exhibits no detectable expression of the gene in a non-hyperproliferative cell. Gene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

In certain embodiments, the recombinant virus is an adenovirus or an adeno-associated virus. In certain embodiments, the recombinant virus is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are recombinant viruses derived from human adenovirus types 2 and 5. Unless stated otherwise, all adenovirus type 5 nucleotide numbers are relative to the NCBI reference sequence AC_000008.1, which is depicted herein in SEQ ID NO: 1.

The adenovirus replication cycle has two phases: an early phase, during which 4 transcription units E1, E2, E3, and E4 are expressed, and a late phase which occurs after the onset of viral DNA synthesis when late transcripts are expressed primarily from the major late promoter (MLP). The late messages encode most of the virus's structural protcins. The gene products of E1, E2 and E4 are responsible for transcriptional activation, cell transformation, viral DNA replication, as well as other viral functions, and are necessary for viral growth.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In certain embodiments, the recombinant virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In certain embodiments, the modification of a regulatory sequence or promoter comprises a modification of sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells, but attenuates expression in normal cells.

In certain embodiments, the modified regulatory sequence is operably linked to a sequence encoding a protein. In certain embodiments, at least one of the adenoviral E1a and E1b genes (coding regions) is operably linked to a modified regulatory sequence. In certain embodiments, the E1a gene is operably linked to the modified regulatory sequence.

The E1a regulatory sequence contains five binding sites for the transcription factor Pea3, designated Pea3 I, Pea3 II, Pea3 III, Pea3 IV, and Pea3 V, where Pea3 I is the Pca3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In certain embodiments, at least one of these seven binding sites, or a functional binding site, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, a recombinant adenovirus, e.g., a recombinant oncolytic adenovirus, comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In certain embodiments, at least one Pea3 binding site, or a functional Pea3 binding site, is deleted. The deleted Pea3 binding site can be Pea3 I, Pea3 II, Pea3 III, Pea3 IV, and/or Pea3 V. In certain embodiments, the deleted Pea3 binding site is Pea3 II, Pea3 III, Pea3 IV, and/or Pea3 V. In certain embodiments, the deleted Pea3 binding site is Pea3 IV and/or Pea3 V. In certain embodiments, the deleted Pea3 binding site is Pea3 II and/or Pea3 III. In certain embodiments, the deleted Pea3 binding site is both Pea3 II and Pea3 III. In certain embodiments, the Pea3 I binding site, or a functional Pea3 I binding site, is retained.

In certain embodiments, at least one E2F binding site, or a functional E2F binding site, is deleted. In certain embodiments, at least one E2F binding site, or a functional E2F binding site, is retained. In certain embodiments, the retained E2F binding site is E2F I and/or E2F II. In certain embodiments, the retained E2F binding site is E2F II. In certain embodiments, the recombinant adenovirus, e.g., recombinant oncolytic adenovirus, may comprise a deletion of at least one E2F binding site, or a functional portion thereof, and not comprise a deletion of a Pea3 binding site. In certain embodiments, the total deletion consists essentially of one or more of Pea3 II, Pea3 III, Pea3 IV, and/or Pea3 V. In certain embodiments, the virus has a deletion of a 50 base pair region located from −304 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 2).

In certain embodiments, a recombinant adenovirus, e.g., a recombinant oncolytic adenovirus, comprises an E1a promoter having a deletion of a functional TATA box, e.g., the deletion of an entire TATA box. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

For example, in certain embodiments, a recombinant adenovirus, e.g., a recombinant oncolytic adenovirus, comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 3), AGTGCCCG (SEQ ID NO: 8), or TATTCCCG (SEQ ID NO: 9), which result from joining the two polynucleotide sequences that would otherwise flank the deleted polynucleotide sequence. In certain embodiments, the virus comprises a polynucleotide deletion that results in a virus comprising the sequence CTAGGACTG (SEQ ID NO: 3), In certain embodiments, a recombinant adenovirus, e.g., a recombinant oncolytic adenovirus, comprises an E1a promoter having a deletion of a functional CAAT box, e.g., the deletion of an entire CAAT box. As used herein, a "functional CAAT box" refers to a CAAT box that is capable of binding to a C/EBP or NF—Y protein, e.g., a CAAT box that has at least 100%, at least 90%, at least 80%, at least 70%, at least 60%, at least 50%, or at least 40%, of the a C/EBP or NF—Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF—Y binding activity of a corresponding wild-type CAAT box sequence. Assays for determining whether a C/EBP or NF—Y protein binds to a CAAT box are known in the art. Exemplary binding assays include electrophoretic mobility shift assays, chromatin immunoprecipitation assays, and DNAse footprinting assays.

For example, in certain embodiments, a recombinant adenovirus, e.g., a recombinant oncolytic adenovirus, comprises a deletion of nucleotides corresponding to −76 to −68 of the adenovirus type 5 E1a promoter, which correspond to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 10), which results from joining the two polynucleotide sequences that would otherwise flank the deleted polynucleotide sequence.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant adenovirus, e.g., a recombinant oncolytic adenovirus, is provided that includes an E1b-19K insertion site, e.g., the recombinant adenovirus has a nucleotide sequence encoding a transgene inserted into an E1b-19K insertion site. In certain embodiments, the insertion site is located between the start site of E1b-19K (i.e., the nucleotide sequence encoding the start codon of E1b-19k, e.g., corresponding to nucleotides 1714-1716 of SEQ ID NO: 1) and the start site of E1b-55K (i.e., the nucleotide sequence encoding the start codon of E1b-55k, e.g., corresponding to nucleotides 2019-2021 of SEQ ID NO: 1). In certain embodiments, the E1b-19K insertion site is located between the start site of E1b-19K (i.e., the nucleotide sequence encoding the start codon of E1b-19k, e.g., corresponding to nucleotides 1714-1716 of SEQ ID NO: 1) and the stop site of E1b-19K (i.e., the nucleotide sequence encoding the stop codon of E1b-19k, e.g., corresponding to nucleotides 2242-2244 of SEQ ID NO: 1).

Throughout the description and claims, an insertion between two sites, for example, an insertion between (i) a start site of a first genc (e.g., E1b-19k) and a start site of a second gene, (e.g., E1b-55K), (ii) a start site of a first gene and a stop site of a second gene, (iii) a stop site of a first gene and start site of a second gene, or (iv) a stop site of first gene and a stop site of a second gene, is understood to mean that all or a portion of the nucleotides constituting a given start site or a stop site surrounding the insertion may be present or absent in the final virus. Similarly, an insertion between two nucleotides is understood to mean that the nucleotides surrounding the insertion may be present or absent in the final virus.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, a nucleotide sequence encoding a transgene is inserted between nucleotides corresponding to 1714 and 1917 or between nucleotides corresponding to 1714 and 1916 of the Ad5 genome (SEQ ID NO: 1). In certain embodiments, a nucleotide sequence encoding a transgene is inserted between CTGACCTC (SEQ ID NO: 4) and TCACCAGG (SEQ ID NO: 5), e.g., the recombinant adenovirus comprises, in a 5' to 3' orientation, CTGACCTC (SEQ ID NO: 4), a nucleotide sequence encoding a transgene, and TCACCAGG (SEQ ID NO: 5). CTGACCTC (SEQ ID NO: 4) and TCACCAGG (SEQ ID NO: 5) define unique boundary sequences for the E1b-19K insertion site within the Ad5 genome (SEQ ID NO: 1). Throughout the description and claims, a deletion adjacent a site, for example, a deletion adjacent a start site of a gene or a deletion adjacent a stop site of a gene, is understood to mean that the deletion may include a deletion of all, a portion, or none of the nucleotides constituting a given start site or a stop site.

In certain embodiments, a recombinant adenovirus, e.g., a recombinant oncolytic adenovirus, is provided that includes an E3 insertion site, e.g., the recombinant adenovirus has a nucleotide sequence encoding a transgene inserted into an E3 insertion site. In certain embodiments, the insertion site is located between the stop site of pVIII (i.e., the nucleotide sequence encoding the stop codon of pVIII, e.g., corresponding to nucleotides 27855-27857 of SEQ ID NO: 1) and the start site of Fiber (i.e., the nucleotide sequence encoding the start codon of Fiber, e.g., corresponding to nucleotides 31042-31044 of SEQ ID NO: 1). In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments, the E3 insertion site is located between the stop site of E3-10.5K (i.e., the nucleotide sequence encoding the stop codon of E3-10.5K, e.g., corresponding to nucleotides 29770-29772 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K. In certain embodiments, the E3 insertion site comprises a deletion of about 1050 nucleotides adjacent the stop site of E3-10.5K, e.g., the E3 insertion site comprises a deletion of 1063 or 1064 nucleotides adjacent the stop site of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or, a nucleotide sequence encoding a transgene is inserted between nucleotides corresponding to 29773 and 30836 of the Ad5 genome (SEQ ID NO: 1). In certain embodiments, a nucleotide sequence encoding a transgene is inserted between CAGTATGA (SEQ ID NO: 11) and TAATAAAAAA (SEQ ID NO: 12), e.g., the recombinant adenovirus comprises, in a 5' to 3' orientation, CAGTATGA (SEQ ID NO: 11), a nucleotide sequence encoding a transgene, and TAATAAAAAA (SEQ ID NO: 12). CAGTATGA (SEQ ID NO: 11) and TAATAAAAAA (SEQ ID NO: 12) define unique boundary sequences for an E3 insertion site within the Ad5 genome (SEQ ID NO: 1).

In certain embodiments, the E3 insertion site is located between stop site of E3-gp19K (i.e., the nucleotide sequence encoding the stop codon of E3-gp19K, e.g., corresponding to nucleotides 29215-29217 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 insertion site comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 insertion site comprises a deletion of about 1600 nucleotides adjacent the stop site of E3-gp19K. e.g., the E3 insertion site comprises a deletion of 1622 nucleotides adjacent the stop site of E3-gp19K. In certain embodiments, the E3 insertion site comprises a deletion corresponding to nucleotides 29218-30839 of the Ad5 genome (SEQ ID NO: 1). In certain embodiments, a nucleotide sequence encoding a transgene is inserted between nucleotides corresponding to 29218 and 30839 of the Ad5 genome (SEQ ID NO: 1). In certain embodiments, a nucleotide sequence encoding a transgene is inserted between TGCCTTAA (SEQ ID NO: 13) and TAAAAAAAAAT (SEQ ID NO: 14), e.g., the recombinant adenovirus comprises, in a 5' to 3' orientation, TGCCTTAA (SEQ ID NO: 13), a nucleotide sequence encoding a transgene, and TAAAAAAAAAT (SEQ ID NO: 14). TGCCTTAA (SEQ ID NO: 13) and TAAAAAAAAAT (SEQ ID NO: 14) define unique boundary sequences for an E3 insertion site within the Ad5 genome (SEQ ID NO: 1).

In certain embodiments, a recombinant adenovirus, e.g., a recombinant oncolytic adenovirus, comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 of the Ad5 genome (SEQ ID NO: 1).

Nucleic acids encoding viral genes can be incorporated into plasmids and introduced into host cells through conventional transfection or transformation techniques. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome). Alternative technologies for the generation of adenovirus include utilization of the bacterial artificial chromosome (BAC) system, in vivo bacterial recombination in a recA=bacterial strain utilizing two plasmids containing complementary adenoviral sequences, and the yeast artificial chromosome (YAC) system.

II. Therapeutic Transgenes

A recombinant virus, e.g., a recombinant oncolytic adenovirus, produced using a method disclosed herein may comprise an exogenous nucleotide sequence that encodes for a therapeutic transgene. The term "transgene" refers to an exogenous gene or polynucleotide sequence. The term "therapeutic transgene" refers to a transgene, which when replicated and/or expressed in or by the virus imparts a therapeutic effect in a target cell, body fluid, tissue, organ, physiological system, or subject.

The therapeutic transgene may encode a therapeutic nucleic acid, e.g., an antisense RNA or ribozyme RNA. The therapeutic transgene may encode a therapeutic peptide or polypeptide, e.g., an apoptotic agent, antibody, CTL responsive peptide, cytokine, cytolytic agent, cytotoxic agent, enzyme, heterologous antigen expressed on the surface of a tumor cell to elicit an immune response, immunostimulatory or immunomodulatory agent, interferon, lytic peptide, oncoprotein, polypeptide which catalyzes processes leading to cell death, polypeptide which complements genetic defects in somatic cells, tumor suppressor protein, vaccine antigen, or any combination thereof.

In certain embodiments, the therapeutic transgene encodes a therapeutic polypeptide selected from CD80, CD137L, IL-23, IL-23A/p19, p40, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

III. Pharmaceutical Compositions

For therapeutic use, a recombinant virus, e.g., a recombinant oncolytic adenovirus, produced using a method disclosed herein is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing recombinant viruses can be presented in a dosage unit form and can be prepared by any suitable method. A pharmaceutical composition should be formulated to be compatible with its intended route of administration. Examples of routes of administration are intravenous (IV), intraarterial, intradermal, inhalation, transdermal, topical, transmucosal, and rectal administration. A preferred route of administration is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethey-lene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant virus) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of the recombinant virus is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the virus, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the virus, and the disease being treated. Exemplary dosing frequencies are once per day, once per week and once every two weeks. A preferred route of administration is parenteral, e.g., intravenous infusion.

IV. Therapeutic Uses

A recombinant virus, e.g., a recombinant oncolytic adenovirus produced using a method disclosed herein, can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, and pancreatic cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In certain embodiments, a recombinant virus, e.g., a recombinant oncolytic adenovirus, is administered to the subject in combination with one or more therapies, e.g., surgery, radiation, chemotherapy, immunotherapy, hormone therapy, or virotherapy. In certain embodiments, a recombinant virus is administered in combination with a tyrosine kinase inhibitor, e.g., erlotinib. In certain embodiments, a recombinant virus of the invention is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab, and BMS 936559 (Bristol Myers Squibb Co.).

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where viruses, compositions and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a virus, a composition, a system, a method, or a process described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

At various places in the present specification, viruses, compositions, systems, processes and methods, or features thereof, are disclosed in groups or in ranges. It is specifically intended that the description include each and every individual subcombination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1: Production of an Oncolytic Adenovirus

This Example describes the production of a recombinant oncolytic adenovirus in A549 cells.

An adenovirus type 5 virus was constructed that carries the deletion of a nucleotide region located from −304 to −255 upstream of the E1a initiation site, which renders E1a expression cancer-selective (as previously described in U.S. Pat. No. 9,073,980). The resulting virus is hereafter referred to as TAV.

TAV was further modified to carry an approximately 200 base pair deletion in the E1b-19k region. The resulting virus is hereafter referred to as TAV-Δ19k. The nucleotide sequence of the modified E1b-19k region is as follows, with residual bases from fused SalI and XhoI sites underlined:

(SEQ ID NO: 6)
ATCTTGGTTACATCTGACCTC<u>GTCGAG</u>TCACCAGGCGCTTTTCCAA

TAV-Δ19k was modified to include a nucleotide sequence encoding a mouse TGF-β trap (a fusion protein of the mouse TGFβ type II receptor and mouse IgG1) in the modified E1b-19k region. The resulting virus is hereafter referred to as TAV-mTGFβ-Trap. The nucleotide sequence encoding the TGF-β trap is as follows:

(SEQ ID NO: 7)
ATGGGTCGGGGCTGCTCCGGGGCCTGTGGCCGCTGCATATCGTCCTGTG

GACGCGCATCGCCAGCACGATCCCGCCGCACGTTCCCAAGTCGGTTAACA

GTGATGTCATGGCCAGCGACAATGGCGGTGCGGTCAAGCTTCCACAGCTG

TGCAAGTTTTGCGATGTGAGACTGTCCACTTGCGACAACCAGAAGTCCTG

CATGAGCAACTGCAGCATCACGGCCATCTGTGAGAAGCCGCATGAAGTCT

GCGTGGCCGTGTGGAGGAAGAACGACAAGAACATTACTCTGGAGACGGTT

TGCCACGACCCCAAGCTCACCTACCACGGCTTCACTCTGGAAGATGCCGC

TTCTCCCAAGTGTGTCATGAAGGAAAAGAAAAGGGCGGGCGAGACTTTCT

TCATGTGTGCCTGTAACATGGAAGAGTGCAACGATTACATCATCTTTTCG

GAAGAATACACCACCAGCAGTCCCGACAGCACCAAGGTGGACAAGAAAAT

TGTGCCCAGGGATTGTGGTTGTAAGCCTTGCATATGTACAGTCCCAGAAG

TATCATCTGTCTTCATCTTCCCCCCAAAGCCCAAGGATGTGCTCACCATT

ACTCTGACTCCTAAGGTCACGTGTGTTGTGGTAGACATCAGCAAGGATGA

TCCCGAGGTCCAGTTCAGCTGGTTTGTAGATGATGTGGAGGTGCACACAG

CTCAGACGCAACCCCGGGAGGAGCAGTTCAACAGCACTTTCCGCTCAGTC

AGTGAACTTCCCATCATGCACCAGGACTGGCTCAATGGCAAGGAGTTCAA

ATGCAGGGTCAACAGTGCAGCTTTCCCTGCCCCCATCGAGAAAACCATCT

CCAAAACCAAAGGCAGACCGAAGGCTCCGCAGGTGTACACCATTCCACCT

CCCAAGGAGCAGATGGCCAAGGATAAAGTCAGTCTGACCTGCATGATAAC

AGACTTCTTCCCTGAAGACATTACTGTGGAGTGGCAGTGGAATGGGCAGC

CAGCGGAGAACTACAAGAACACTCAGCCCATCATGGACACAGATGGCTCT

TACTTCGTCTACAGCAAGCTCAATGTGCAGAAGAGCAACTGGGAGGCAGG

AAATACTTTCACCTGCTCTGTGTTACATGAGGGCCTGCACAACCACCATA

CTGAGAAGAGCCTCTCCCACTCTCCTGGTAAATGA

SF-BMAdR 281 A549 cells (purchased from National Research Council of Canada) were cultured in serum-free media (Hyclone SFM4Transfx-293) in suspension culture in shake flasks. After growth to a density of 2×10⁶ cells/mL in a total volume of 100 mL, the cells were centrifuged and resuspended in 100 mL of fresh SFM4Transfx-293 media. 50 mL of the resuspended culture was infected with the TAV-Δ19k adenovirus, and 50 mL of the resuspended culture was infected with the TAV-mTGFβ-Trap adenovirus. The cells were maintained in suspension culture in shake flasks for three days to allow for viral replication, and the cultures were then lysed with freeze-thaw cycles to produce cell lysate.

The viruses were then purified from the cell lysate by centrifugation, nuclease treatment, anion exchange chromatography, and dialysis into a buffer appropriate for in vivo administration (10 mM Tris, 1 mM $MgCl_2$, 3% sucrose, pH 8).

Figure 2:
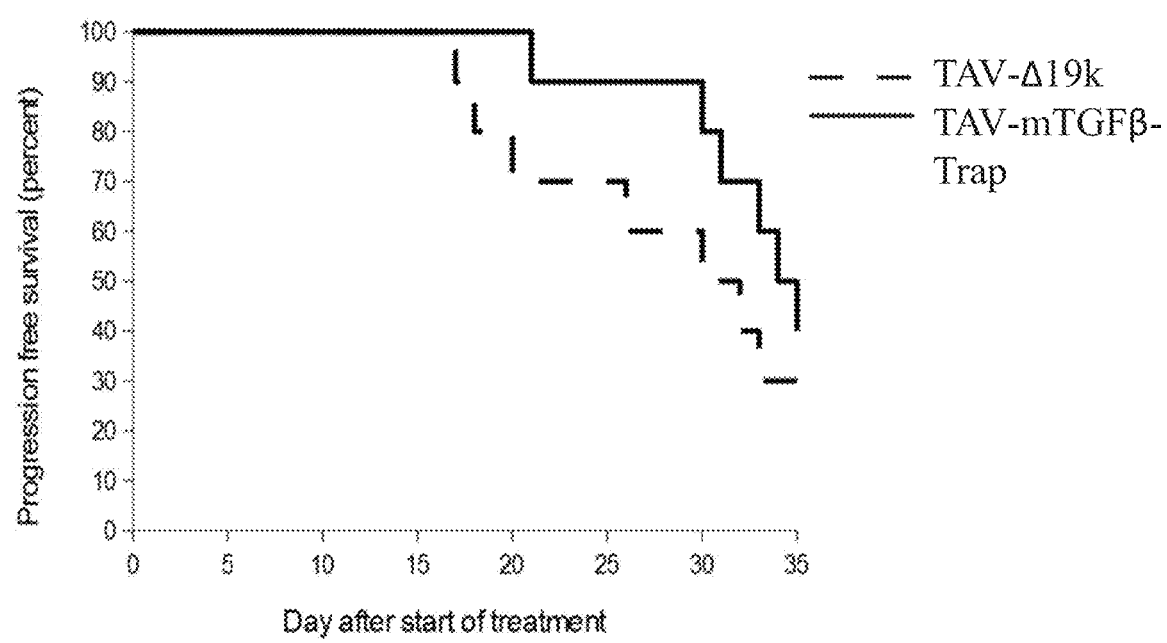
FIG. 2 is a line graph depicting progression free survival of mice treated with the indicated virus. Progression is defined as tumor volume exceeding 200 mm3.

The viruses were then tested for efficacy in vivo. Adult 129S4 mice were injected subcutaneously with $1\times10^6$ ADS-12 cells, a pulmonary cancer cell line, and allowed to form subcutaneous tumors. After the tumors grew large enough to treat, 10 mice each were treated with intratumoral injections of either the TAV-Δ19k adenovirus or the TAV-mTGFβ-Trap adenovirus. Three doses of $1\times10^9$ IU of each virus were administered every four days. Mean tumor volume in mice treated with each virus is depicted in FIG. 1, and progression free survival of mice treated with each virus is depicted in FIG. 2.

Example 2: Production of an Oncolytic Adenovirus

This Example describes the production of a recombinant oncolytic adenovirus in A549 derived cells relative to HEK-293 derivedcells.

An adenovirus type 5 virus was constructed that carries the deletion of a nucleotide region located from −304 to −255 upstream of the E1a initiation site, which renders E1a expression cancer-selective (as previously described in U.S. Pat. No. 9,073,980). The resulting virus is hereafter referred to as TAV.

TAV was further modified to carry an approximately 200 base pair deletion in the E1b-19k region. The resulting virus is hereafter referred to as TAV-Δ19k. The nucleotide sequence of the modified E1b-19k region is as follows, with residual bases from fused SalI and XhoI sites underlined:

(SEQ ID NO: 6)
ATCTTGGTTACATCTGACCTCGTCGAGTCACCAGGCGCTTTTCCAA

TAV-Δ19k was modified to include a nucleotide sequence encoding a human TGF-β trap (a fusion protein of the human TGFß type II receptor and human IgG1) in the modified E1b-19k region. The resulting virus is hereafter referred to as TAV-hTGFβ-Trap.

Figure 3:
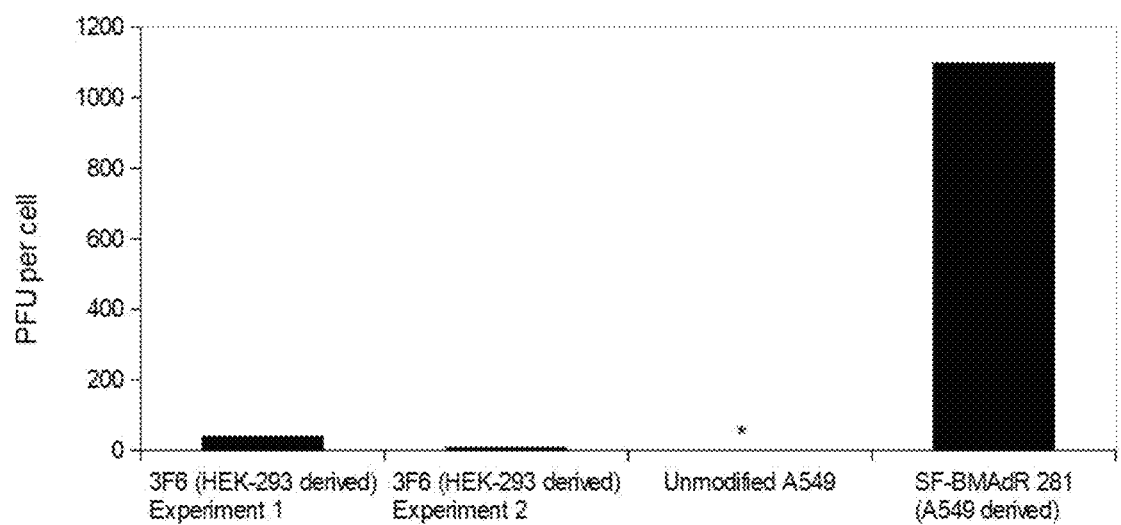
FIG. 3 depicts viral production from a HEK-293 derived cell line and the SF-BMAdR 281 (A549 derived) cell line. No results were available for unmodified A549 cells because they could not be adapted to serum-free suspension culture.

TAV-hTGFβ-Trap adenovirus was produced in both HEK-293 cells (293-3F6) and A549 cells (SF-BMAdR). HEK-293 cells cultured in serum-free medium (SFM4Transfx-293) at $5\times10^5$ cells/mL were infected with TAV-hTGFβ-Trap at a multiplicity of infection (MOI) of 3. At 4 days post-infection the yield was 42 PFU/cell. In a separate experiment, HEK-293 cells cultured in serum-free medium (SFM4Transfx-293) at $1\times10^6$ cells/mL were infected with TAV-hTGFβ-Trap at an MOI of 3. At 4 days post-infection the yield was less than 10 PFU/cell. A549 cells cultured in serum-free medium (SFM4Transfx-293) at $1\times10^6$ cells/mL were infected with TAV-hTGFβ-Trap at an MOI of 3. At 4 days post-infection the yield was 1100 PFU/cell. Unmodified A549 cells could not be adapted to grow in the same serum-free medium (SFM4Transfx-293) in suspension culture. Viral production from these cell lines is depicted in FIG. 3.

Together, these results show that A549 derived host cells, e.g., SF-BMAdR A549 host cells, produce greater yields of certain oncolytic viruses, e.g., the TAV-hTGFβ-Trap adenovirus.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. A composition comprising an A549 host cell adapted to suspension culturing in a serum-free medium infected with a recombinant oncolytic adenovirus,
   wherein the recombinant oncolytic adenovirus comprises an E1a gene comprising an E1a protein coding region operably linked to a modified regulatory sequence comprising (i) deletion of a functional Pea3 binding site, (ii) deletion of a functional E2F binding site, (iii) deletion of a functional TATA box, (iv) deletion of a functional CAAT box, (v) deletion of the nucleotides corresponding to the nucleotides from 195-244 of the Ad5 genome (SEQ ID NO: 1), or (vi) has two, three, or four of (i), (ii), (iii), and (iv).

2. The composition of claim 1, wherein the recombinant oncolytic adenovirus is a type 5 adenovirus (Ad5).

3. The composition of claim 1, wherein the A549 host cell is a SF-BMAdR 281 A549 cell.

4. The composition of claim 1, wherein the A549 host cell is cultured for at least 3 days.

5. The composition of claim 1, further comprising, after step (b), the step of purifying the recombinant oncolytic adenovirus.

6. The composition of claim 5, wherein the step of purifying the recombinant oncolytic adenovirus comprises lysing the A549 host cell.

7. The composition of claim 5, wherein the step of purifying the recombinant oncolytic adenovirus comprises nuclease treatment.

8. The composition of claim 5, wherein the step of purifying the recombinant oncolytic adenovirus comprises ion exchange chromatography.

9. The composition of claim 8, wherein the step of purifying the recombinant oncolytic adenovirus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography.

10. The composition of claim 1, wherein the E1a promoter has the deletion of a functional Pea3 binding site.

11. The composition of claim 1, wherein the E1a promoter has the deletion of a functional TATA box.

12. The composition of claim 1, wherein the recombinant oncolytic adenovirus comprises a polynucleotide deletion that results in a virus sequence comprising the junction sequence corresponding to CTAGGACTG (SEQ ID NO: 3), AGTGCCCG (SEQ ID NO: 8) and/or TATTCCCG (SEQ ID NO: 9) of the Ad5 genome (SEQ ID NO: 1).

13. The composition of claim 1, wherein the E1a promoter has the deletion of a functional CAAT box.

14. The composition of claim 1, wherein the recombinant oncolytic adenovirus comprises a nucleotide sequence encoding a transgene.

15. The composition of claim 14, wherein the nucleotide sequence is inserted into an E1b-19K insertion site, and wherein the E1b-19K insertion site is located between the start site of E1b-19K and the stop site of E1b-19K.

16. The composition of claim 14, wherein the transgene is not operably linked to an exogenous promoter sequence and/or the recombinant virus selectively expresses the transgene in a hyperproliferative cell.

17. The composition of claim 14, wherein the transgene encodes a polypeptide selected from CD80, CD137L, IL-23, IL-23A/p19, p40, IL-27, IL-27A/p28, IL-27B/EBI3, ICAM-1, a TGF-β Trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

18. The composition of claim 1, wherein the Pea3 binding site is selected from Pea3 I, Pea3 II, Pea3 III, Pea3 IV, and Pea3 V.

19. The composition of claim 1, wherein the E2F binding site is selected from E2F I and E2F II.

* * * * *

SEQUENCE LISTING

```
Sequence total quantity: 14
SEQ ID NO: 1            moltype = DNA  length = 35938
FEATURE                 Location/Qualifiers
source                  1..35938
                        mol_type = unassigned DNA
                        organism = Adenovirus type 5
SEQUENCE: 1
catcatcaat aatataccct attttggatt gaagccaata tgataatgag ggggtggagt   60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgttttg   180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tatttgtcta gggccgcggg  360
gactttgacc gtttacgtgg agactcgccc aggtgttttt ctcaggtgtt ttccgcgttc  420
cgggtcaaag ttggcgtttt attattatag tcagctgacg tgtagtgtat ttatacccgg  480
tgagttcctc aagaggccac tcttgagtgc cagcgagtag agttttctcc tccgagccgc  540
tccgacaccg ggactgaaaa tgagacatat tatctgccac ggaggtgtta ttaccgaaga  600
aatggccgcc agtcttttgg accagctgat cgaagaggta ctggctgata atcttccacc  660
```

```
tcctagccat tttgaaccac ctacccttca cgaactgtat gatttagacg tgacggcccc   720
cgaagatccc aacgaggagg cggtttcgca gattttccc gactctgtaa tgttggcggt    780
gcaggaaggg attgacttac tcactttcc gccggcgccc ggttctccgg agccgcctca   840
cctttccgg cagcccgagc agccggagca gagagccttg ggtccggttt ctatgccaaa    900
ccttgtaccg gaggtgatcg atcttacctg ccacgaggct ggctttccac ccagtgacga   960
cgaggatgaa gagggtgagg agtttgtgtt agattatgtg gagcaccccg ggcacggttg  1020
caggtcttgt cattatcacc ggaggaatac gggggaccca gatattatgt gttcgctttg  1080
ctatatgagg acctgtggca tgtttgtcta cagtaagtga aaattatggg cagtgggtga  1140
tagagtggtg ggtttggtgt ggtaattttt tttttaattt ttacagtttt gtggtttaaa  1200
gaattttgta ttgtgatttt tttaaaaggt cctgtgtctg aacctgagcc tgagcccgag  1260
ccagaaccgg agcctgcaag acctacccgc cgtcctaaaa tggcgcctgc tatcctgaga  1320
cgcccgacat cacctgtgtc tagagaatgc aatagtagta cggatagctg tgactccggt  1380
ccttctaaca cacctcctga gatacacccg gtggtcccgc tgtgccccat taaaccagtt  1440
gccgtgagag ttggtgggcg tcgccaggct gtggaatgta tcgaggactt gcttaacgag  1500
cctgggcaac ctttggactt gagctgtaaa cgcccaggc cataaggtgt aaacctgtga   1560
ttgcgtgtgt ggttaacgcc tttgtttgct gaatgagttg atgtaagttt aataaagggt  1620
gagataatgt ttaacttgca tggcgtgtta aatggggcgg ggcttaaagg gtatataatg  1680
cgccgtgggc taatcttggt tacatctgac ctcatggagg cttgggagtg tttggaagat  1740
ttttctgctg tgcgtaactt gctggaacag agctctaaca gtacctcttg gttttggagg  1800
tttctgtggg gctcatccca ggcaaagtta gtctgcagaa ttaaggagga ttacaagtgg  1860
gaatttgaag agcttttgaa atcctgtggt gagctgtttg attctttgaa tctgggtcac  1920
caggcgcttt tccaagagaa ggtcatcaag acttttgagt tttccacacc ggggcgcgct  1980
gcggctgctg ttgctttttt gagttttata aaggataaat ggagcgaaga aacccatctg  2040
agcgggggt acctgctgga ttttctggcc atgcatctgt ggagagcggt tgtgagacac   2100
aagaatcgcc tgctactgtt gtcttccgtc cgcccggcga taataccgac ggaggagcag  2160
cagcagcagc aggaggaagc caggcggcgg cggcaggago agagcccatg gaacccgaga  2220
gccggcctgg accctcggga atgaatgttg tacaggtggc tgaactgtat ccagaactga  2280
gacgcatttt gacaattaca gaggatgggc aggggctaaa gggggtaaag agggagcggg  2340
gggcttgtga ggctacagag gaggctagga atctagcttt tagcttaatg accagacacc  2400
gtcctgagtg tattacttt caacagatca aggataattg cgctaatgac cttgatctgc   2460
tggcgcagaa gtattccata agcagctga ccacttactg gctgcagcca ggggatgatt   2520
ttgaggaggc tattagggta tatgcaaagg tggcacttag gccagattgc aagtacaaga  2580
tcagcaaact tgtaaatatc aggaattgtt gctacatttc tgggaacggg gccgaggtgg  2640
agatagatac ggaggatagg gtgccttta gatgtagcat gataaatatg tggccgggg    2700
tgcttggcat ggacggggtg gttattatga atgtaaggtt tactggcccc aattttagcg  2760
gtacggtttt cctggccaat accaacctta tcctacacgg tgtaagcttc tatgggttta  2820
acaatacctg tgtggaagcc tggaccgatg taagggttcg gggctgtgcc ttttactgct  2880
gctggaaggg ggtggtgtgt cgccccaaaa gcagggcttc aattaagaaa tgcctctttg  2940
aaaggtgtac cttgggtatc ctgtctgagg gtaactccag ggtgcgccac aatgtgcgct  3000
ccgactgtgg ttgcttcatg ctagtgaaaa gcgtggctgt gattaagcat aacatgtgta  3060
gtggcaactg cgaggacagg gcctctcaga tgctgacctg ctcggacggc aactgtcacc  3120
tgctgaagac cattcacgta gccagccact ctcgcaaggc ctggcagtg tttgagcata   3180
acatactgac ccgctgttcc ttgcatttgg gtaacaggag ggggtgttc ctaccttacc   3240
aatgcaattt gagtcacact aagatattgc ttgagcccga gagcatgtcc aaggtgaacc  3300
tgaacggggt gtttgacatg accatgaaga tctggaaggt gctgaggtac gatgagaccc  3360
gcaccaggtg cagaccctgc gagtgtgcg gtaaacatat taggaaccag cctgtgatgc   3420
tggatgtgac cgaggagctg aggcccgatc acttggtgct ggcctgccac cgcgctgagt  3480
ttggctctag cgatgaagat acagattgag gtactgaaat gtgtgggcgt ggcttaaggg  3540
tgggaaagaa tatataaggt gggggtctta tgtagttttg tatctgtttt gcagcagccg  3600
ccgccgccat gagcaccaac tcgtttgatg gaagcattgt gagctcatat ttgacaacgc  3660
gcatgccccc atgggcgggg gtgcgtcaga atgtgatggg ctccagcatt gatgctgcc   3720
ccgtcctgcc cgcaaactct actaccttga cctacgagac cgtgtctgga acgccgttgc  3780
agactgcagc ctccgccgcc gcttcagccg ctgcagccac cgcccgcggg attgtgactg  3840
actttgcttt cctgagcccg cttgcaagca gtgcagcttc ccgttcatcc gcccgcgatg  3900
acaagttgac ggctctttg gcacaattgg atttctttga ccgggaactt aatgtcgttt   3960
ctcagcagct gttggatctg cgccagcagg tttctgccct gaaggcttcc tcccctccca  4020
atgcggttta aacataaat aaaaaaccag actctgtttg gatttggatc aagcaagtgt   4080
cttgctgtct ttatttaggg gttttgcgcg cgcggtaggc ccgggaccag cggtctcggt  4140
cgttgagggt cctgtgtatt ttttccagga cgtggtaaag gtgactctgg atgttcagat  4200
acatgggcat aagcccgtct ctggggtgga ggtagcacca ctgcagagct tcatgctgcg  4260
gggtggtgtt gtagatgatc cagtcgtagc aggagcgctg ggcgtggtgc ctaaaaatgt  4320
cttttcagtag caagctgatt gccaggggca ggccctggt gtaagtgttt acaaagcggt   4380
taagctggga tgggtgcata cgtggggata tgagatgcat cttggactgt attttaggt   4440
tggctatgtt cccagccata tccctccggg gattcatgtt gtgcagaacc accagcacag  4500
tgtatccggt gcacttggga aatttgtcat gtagcttaga aggaaatgcg tggaagaact  4560
tggagacgcc cttgtgacct ccaagatttt ccatgcattc gtccataatg atggcaatgg  4620
gcccacgggg ggcggcctgg gcgaagatat ttctgggatc actaacgtca tagttgtgtt  4680
ccaggatgag atcgtcatag gccattttta caaagcgcg gcggagggtg ccagactgcg  4740
gtataatggt tccatccggc ccaggggcgt agttaccctc acagattttgc atttcccacg  4800
ctttgagttc agatgggggg atcatgtcta cctgcggggc gatgaagaaa acggtttccg  4860
gggtagggga gatcagctgg gaagaaagca ggttcctgag cagctgcgac ttaccgcagc  4920
cggtgggccc gtaaatcaca cctattaccg ggtgcaactg gtagtaagag agctgcagc   4980
tgccgtcatc cctgagcagg ggggccactt cgttaagcat gtccctgact cgcatgtttt  5040
ccctgaccaa atccgccaga aggcgctcgc cgccacgaca tagcagttct tgcaaggaag  5100
caaagttttt caacggtttg agaccgtccg ccgtaggcat gctttgagc gtttgaccaa   5160
gcagttccag gcggtcccac agctcggtca cctgctctac ggcatctcga tccagcatat  5220
ctcctcgttt cgcgggttgg ggcggctttc gctgtacggc agtagtcggt gctcgtccag  5280
acgggccagg gtcatgtctt tccacggggcg cagggtcctc gtcagcgtag tctgggtcac  5340
ggtgaagggg tgcgctccgg gctgcgcgct ggccagggtg cgcttgaggc tggtcctgct  5400
```

```
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaaactcgga cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa gggggggctat aaaaggggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgaggggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtcac   6420
gcgccaaccg cggttgtgca gggtgacaag gtcaacgctg ggctaccct ctccgcgtag   6480
gcgctcgttg gtccagcaga ggcggccgcc cttgcgcgag cagaatgcg gtaggggggtc   6540
tagctgcgtc tcgtccgggg ggtctgcgtc acggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtgggggg accccatggc atggggtggt tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttgaagct tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa ggtaagagc ctagcatgta   7200
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgcttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtc   7500
aattacctgg gcgcgcagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattage atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag aacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgaagcc ctcgcctggc ggtttggct ggtggtcttc   8220
tacttcggct gcttgtcctt gaccgtctgg ctgctcgagg ggagttacgg tggatcggac   8280
caccacgccg cgcgagccca agtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcaggggcg cgggctagat ccaggtgata   8460
cctaattccc aggggctggt tggtggcggc gtcgatggct tgcaagaggc cgcatcccccg   8520
cggcgcgact acggtaccgc gcggcgggcg gtgggccgcg gggtgtcct tggatgatgc   8580
atctaaaagc ggtgacgcgg gcgagccccc ggaggtaggg ggggctccgg acccgccggg   8640
agaggggca gggcacgtc ggcgccgcgc gcgggcaggg gctggtgctg cgcgctagg   8700
ttgctggcga acgcgacgac gcggcggttg atctcctgaa tctgcgcct ctgcgtgaag   8760
acgacgggcc cggtgagctt gagcctgaaa gagagttcga cagaatcaat ttcggtgtcg   8820
ttgacgcgg cctggcgcaa aatctcctgc acgtctcctg agttgtcttg ataggcgatc   8880
tcggccatga actgctcgat tcttcctcc tggagatctc cgcgtccggc tcgctccacg   8940
gtgccggga ggtcgttgga aatgcgggc atgagctgcg agaaggcgtt gaggcctccc   9000
tcgttccaga cgcggctgta gaccacgccc ccttcggcat cgcggggccg catgaccacc   9060
tgcgcgagat tgagctccac gtgccgggcg aagacgcgt agtttcgcag gcgctgaaag   9120
aggtagttga ggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataaggggcc tcccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacgggca gcggggggcg   9540
agttggaaga cgccgcccgt catgtccccgg ttatggggttg gcgggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcggcggca gcggcggcg gtcggggttg   9780
tttctggcgg aggtgctgct gatgatgtaa ttaaagtagg cgttcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcttttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
```

```
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagagggcg   10380
cagcgtaggg tggccggggc tccggggcg agatcttcca acataaggcg atgatatcg   10440
tagatgtacc tggacatcca ggtgatgccg gcgcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttccttcc aggcgcggcg   10800
gctgctgcgc tagcttttt ggccactggc cgcgcgcagc gtaagcggtt aggctggaaa   10860
gcgaaagcat taagtggctc gctccctgta gccggaggt tattttccaa gggttgagtc   10920
gcgggacccc cggttcgagt ctcggaccgg ccggactgcg gcgaacgggg gtttgcctcc   10980
ccgtcatgca agaccccgct tgcaaattcc tccggaaaca gggacgagcc cctttttgc   11040
ttttcccaga tgcatccggt gctgcggcag atgcgccccc ctcctcagca gcggcaagag   11100
caagagcagc ggcagacatg cagggcaccc tccctcctc ctaccgcgtc aggaggggcg   11160
acatccgcgg ttgacggc agcagatggt gattacgaac ccccgcggcg ccgggcccgg   11220
cactacctgg acttggagga gggcgagggc ctgcgcgcgc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc caagatata ccatacccct tacgttccca tagacaagga ggtaaagatc   11940
gagggggttct acatgcgcat ggcgctgaag gtgcttacct tgagcgacga cctgggcgtt   12000
tatcgcaacg agcgcatcca aaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggcggacc tgggctggcg gtggcaccg gcgcgcgctg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcacga aaccggctct aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accgctggt gggggatgtg cgcgaggccg tggcgcagg tggcgcagg cagcagcagg   12720
gcaacctggg ctccatggtt gcactaaacg ccttcctgag tacacagccc gccaacgtgc   12780
cgcggggaca ggaggactac accaactttt gagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcagggggctg tgggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
tccaggagat tacaagtgtc agccgcgcgc tgggcagga ggacacgggc agcctggagg   13200
caaccctaaa ctacctgctg accaaccggc ggcagaagat cccctcgttg cacagtttaa   13260
acagcgagga ggagcgcatt ttgcgctacg tgcagcagag cgtgagcctt aacctgatgc   13320
gcgacgggt aacgcccagc gtggcgctgg acatgaccgc gcgcaacatg gaaccgggca   13380
tgtatgcctc aaaccggccg tttatcaacc gcctaatgaa ctacttgcat cgcgccggcg   13440
ccgtgaaccc cgagtatttc accaatgcca tcttgaaccc gcactggcta ccgcccctg   13500
gtttctacac cggggattc gaggtgcccg agggtaacga tggattcctc tgggacgaca   13560
tagacgacag cgtgttttcc ccgcaaccgc agacctgct agagttgcaa cagcgcgagc   13620
aggcagagcc ggcgctgcga aaggaaagct tccgcaggcc aagcagcttg tccgatctag   13680
gcgctgcggc cccgcggtca gatgctagta gcccattcc aagcttgata gggtctctta   13740
ccagcactcg caccacccgc ccgcgcctgc tgggcgagga ggagtaccta aacaactcgc   13800
tgctgcagcc gcagcgcgaa aaaaacctgc ctccggcatt tcccaacaac gggatagaga   13860
gcctagtgga caagatgagt agatggaaga cgtacgcgca ggagcacagg gacgtgccag   13920
gcccgcgccc gccaccgt cgtcaaaggc acgaccgtca gcgggggtctg gtgtgggagg   13980
acgatgactc ggcagacgac agcagcgtcc tggattgggg agggagtggc aacccgtttg   14040
cgcaccttcg ccccaggctg gggagaatgt tttaaaaaaa aaaagcatg atgcaaaata   14100
aaaaactcac caaggccatg gcaccgagcg ttggttttct tgtattcccc ttagtatgcg   14160
gcgcgcggcg atgtatgagg aaggtcctcc tccctcctac gagagtgtgg tgagcgcggc   14220
gccagtgcgg gcggcgctgg gttctccctt cgatgctcca ctggaccgc cgtttgtcc   14280
tccgcggtac ctgcggccta ccgggggggag aaacagcatc cgttactctg agttggcacc   14340
cctattcgac accaccccgtg tgtacctggt ggacaacaag tcaacggatg tggcatccct   14400
gaactaccag aacgaccaca gcaacttct gaccacggtc attcaaaaca atgactacag   14460
cccgggggag gcaagcacac agaccatcaa tcttgacgac cggtcgcact ggggcggcga   14520
cctgaaaacc atcctgcata caactgcc aaatgtgaac gagttcatgt ttaccaataa   14580
gtttaaggcg cgggtgatgg tgtcgcgctt gcctactaag gacaatcagg tggagctgaa   14640
atacgagtgg gtgagttca cgctgcccga gggcaactac tccgagacca tgaccataga   14700
ccttatgaac aacgcgatcg tggagcacta cttgaaagtg gcagacaga acggggttct   14760
ggaaagcgac atcgggtaa agtttgacac ccgcaacttc agactggggt ttgaccccgt   14820
cactggtctt gtcatgcctg gggtatatac aaacgaagcc ttccatccag acatcatttt   14880
```

```
gctgccagga tgcggggtgg acttcaccca cagccgcctg agcaacttgt tgggcatccg   14940
caagcggcaa cccttccagg agggctttag gatcacctac gatgatctgg agggtggtaa   15000
cattcccgca ctgttggatg tggacgccta ccaggcgagc ttgaaagatg acaccgaaca   15060
gggcgggggt ggcgcaggcg gcagcaacag cagtggcagc ggcgcggaag agaactccaa   15120
cgcggcagcc gcggcaatgc agccggtgga ggacatgaac gatcatgcca ttcgcggcga   15180
cacctttgcc acacgggctg aggagaagcc cgctgaggcc gaagcagcgg ccgaagctgc   15240
cgcccccgct gcgcaacccg aggtcgagaa gcctcagaag aaaccggtga tcaaaccccct   15300
gacagaggac agcaagaaac gcagttacaa cctaataagc aatgacagca ccttcaccca   15360
gtaccgcagc tggtaccttg catacaacta cggcgacccet cagaccggaa tccgctcatg   15420
gaccctgctt tgcactcctg acgtaacctg cggctcggag caggtctact ggtcgttgcc   15480
agacatgatg caagaccccg tgaccttccg ctccacgcgc cagatcagca actttccggt   15540
ggtgggcgcc gagctgttgc ccgtgcactc caagagcttc tacaacgacc aggccgtcta   15600
ctcccaactc atccgccagt ttacctctct gacccacgtg ttcaatcgct ttcccgagaa   15660
ccagattttg gcgcgcccgc cagccccac catcaccacc gtcagtgaaa acgttcctgc   15720
tctcacagat cacgggacgc taccgctgcg caacagcatc ggaggagtcc agcgagtgac   15780
cattactgac gccagacgcc gcacctgccc ctacgtttac aagccctggg gcatagtctc   15840
gccgcgcgtc ctatcgagcc gcacttttttg agcaagcatg tccatcctta tatcgcccag   15900
caataacaca ggctggggcc tgcgcttccc aagcaagatg tttggcgggg ccaagaagcg   15960
ctccgaccaa cacccagtgc gcgtgcgcgg gcactaccgc gcgccctggg gcgcgcacaa   16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
ggtgcgggga gcccggcgct atgctaaaat gaagagacgg cggaggcgcg tagcacgtcg   16200
ccaccgccgc cgaccggcca ctgccgccca acgcgcggcg gcggcctgc ttaaccgcgc   16260
acgtcgcacc ggccgacggg cggccatgcg ggccgctcga aggctggccg cgggtattgt   16320
cactgtgccc cccaggtcca ggcgacgagc ggccgccgca gcagccgcgg ccattagtgc   16380
tatgactcag ggtcgcaggg gcaacggtgt attgggtgcc gactcggtta ggggcctgcg   16440
cgtgcccgtg cgcaccccgc ccccgcgcaa ctagattgca agaaaaaact acttagactc   16500
gtactgttgt atgtatccag cggcggcggc gcgcaacgaa gctatgtcca agcgcaaaat   16560
caaagaagag atgctccagg tcatcgcgcc ggagatctat ggccccccga agaaggaaga   16620
gcaggattac aagccccgaa agctaaagcg ggtcaaaaag aaaaagaaag atgatgatga   16680
tgaacttgac gacgaggtgg aactgctgca cgctaccgcg cccaggcgac gggtacagtg   16740
gaaaggtcga cgcgtaaaac gtgttttgcg acccggcacc accgtagtct ttacgcccgg   16800
tgagcgctcc acccgcacct acaagcgcgt gtatgatgag gtgtacgcg acgaggacct   16860
gcttgagcga gccaacgagc gcctcgggga gtttgcctac ggaaagcggc ataaggacat   16920
gctggcgttg ccgctggacg agggcaaccc aaccacctag ctaaagccg taacactgca   16980
gcaggtgctg cccgcgcttg caccgtccga agaaaagcgc ggcctaaagc gcgagtctgg   17040
tgacttggca cccaccgtgc agctgatggt acccaagcgc cagcgactgg aagatgtctt   17100
ggaaaaaatg accgtggaac ctgggctgga gcccgaggtc cgcgtgcggc caatcaagca   17160
ggtggcgcgg ggactgggcg tgcagacgcgt ggacgttcag ataccccacta ccagtagcac   17220
cagtattgcc accgccacag agggcatgga gacacaaacg tccccggttg cctcagcggt   17280
ggcggatgcc gcggtgcagg cggtcgctgc ggccgcgtcc aagacctcta cggaggtgca   17340
aacggacccg tggatgtttc gcgtttcagc ccccgcgc ccgcgcggtt cgaggaagta   17400
cggcgcgcc agcgcgctac tgcccgaata tgccctacat ccttccattg cgcctacccc   17460
cggctatcgt ggctacacct accgccccag aagacgagca actacccgac gccgaaccac   17520
cactggaacc cgccgccgcc gtcgccgtcg ccagcccgtg ctggcccga tttccgtgcg   17580
cagggtggct cgcgaaggag gcaggaccct ggtgctgcca acagcgcgct accacccccag   17640
catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg cgccgtgcc   17880
cggaattgca tccgtggcct tgcaggcgca gagacactga ttaaaaacaa gttgcatgtg   17940
gaaaaatcaa aataaaaagt ctggactctc acgctcgctt ggtcctgtaa ctattttgta   18000
gaatggaaga catcaacttt gcgtctctgg ccccgcgaca cggctcgcgc ccgttcatgg   18060
gaaactggca agatatcggc accagcaata tgagcggtgg cgccttcagc tggggctcgc   18120
tgtggaggca cattaaaaat ttcggttcca ccgttaaaga ctatgcagc aaggcctgga   18180
acagcagcac aggccagatg ctgagggata agttgaaaga gcaaaatttc caacaaaagg   18240
tggtagatgg cctggcctct ggcattagcg gggtggtgga cctggccaac caggcagtgc   18300
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagctccct cgtacgagga ggcactaaag caaggcctgc   18480
ccaccacccg tccatcgcg cccatggcta ccggagtgct gggccagcac acacccgtaa   18540
cgctggacct gcctccccc gccgacaccc agcagaaacc tgtgctgcca ggcccgaccg   18600
ccgttgttgt aaccccgtcct agccgcgcgt ccctgcgccg cgccgccagc ggtccgcgat   18660
cgttggcc cgtagccagt ggcaactggc aaagcaccat gaacagctac gtgggctgg   18720
gggtgcaatc cctgaagcgc cgacgatgct tctgaatagc taacgtgtcg tatgtgtgtc   18780
atgtatcgt ccatgtcgcc gccagaggag ctgctgagcc gccgcgcgcc cgctttccaa   18840
gatggctacc ccttcgatga tgccgcagtg gtcttacatg cacatctcgg gccaggacgc   18900
ctcggagtac ctgagcccg gctggtgca gtttgcccgc gccaccgaga cgtacttcag   18960
cctgaataac aagtttagaa accccacggt ggcgcctaca cacgacgtgg ccacagacga   19020
gtcccagcgt ttgacgctgc ggttcatccc tgtggaccgt gaggatactg cgtactcgta   19080
caaggcgcgg ttcaccctag ctgtgggtga taaccgtgtg ctggacatgg cttccacgta   19140
ctttgacatc cgcggcgtgc tggacagggg ccctacttt aagccctact ctggcactgc   19200
ctacaacgcc ctggctccca agggtgcccc aaatccttgc gaatgggatg aagctgctac   19260
tgctcttgaa ataaacctag aagaagagga cgatgacgaa gagacgagca   19320
agctgagcag caaaaaactc acgtatttgg gcaggcgcct tattctggta taaattattac   19380
aaaggagggt attcaaatag gtgtcgaagg tcaaacacct aaatatgccg ataaaacatt   19440
tcaacctgaa cctcaaatag gagaatctca gtggtacgaa actgaaatta tcatgcagc   19500
tgggagagtc cttaaaaaga ctaccccaat gaaaccatgt tacggttcat atgcaaaacc   19560
cacaaatgaa aatggagggc aaggcattct tgtaaagcaa caaaatggaa agctagaaag   19620
```

```
tcaagtggaa atgcaatttt tctcaactac tgaggcgacc gcaggcaatg gtgataactt   19680
gactcctaaa gtggtattgt acagtgaaga tgtagatata gaaacccag acactcatat    19740
ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttgaaata attttgccat    20220
ggaaatcaat ctaaatgcca acctgtggag aaatttcctg tactccaaca tagcgctgta   20280
tttgcccgac aagctaaagt acagtccttc caacgtaaaa atttctgata cccaaacac    20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgccttttacg ccaccttctt   20700
ccccatggcc cacaacaccg cctccacgct tgaggcatg cttagaaacg acaccaacga    20760
ccagtccttt aacgactatc tctccgccgc caacatgctc tacccctatac ccgccaacgc   20820
taccaacgtg cccatatcca tccctcccg caactgggcg gcttccgcg gctgggcctt     20880
cacgcgcctt aagactaagg aaaccccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgcaaact ccgcccacgc   21540
gctagacatg acttttgagg tggatcccat ggacgagccc accttctttt atgttttgtt   21600
tgaagtcttt gacgtggtcc gtgtgacccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat attttttggg cacctatgac aagcgctttc caggctttgt ttctccacac   21840
aagctcgcct gcgccatagt caatacggcc ggtcgcgaga ctgggggcgt acactggatg   21900
gcctttgcct ggaacccgca ctcaaaaaca tgctacctct ttgagccctt tggctttttct  21960
gaccagcgac tcaagcaggt ttaccagttt gagtacgagt cactcctgcg ccgtagcgcc   22020
attgcttctt cccccgaccg ctgtataacg ctggaaaagt ccaccaaag cgtacagggg    22080
cccaactcgg ccgcctgtgg actattctgc tgcatgtttc tccacgcctt tgccaactgg   22140
cccaaaactc ccatggatca caacccccacc atgaaccta ttaccggggt acccaactcc     22200
atgctcaaca gtccccaggt acagcccacc ctgcgtcgca accaggaaca gctctacagc   22260
ttcctggagc gccactcgcc ctacttcgc agccacagtg cgcagattag gagcgccact   22320
tctttttgtc acttgaaaaa catgtaaaaa taatgtacta gagacacttt caataaaggc   22380
aaatgctttt atttgtacac tctcgggtga ttatttacac ccacccttcc cgtctgcgcc   22440
gtttaaaaat caaagggggtt ctgccgcgca tcgctatgcg ccactggcag ggacacgttg    22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
cagcactgga acactatcag cgccgggtgg tgcacgctgg ccagcacgct cttgtcggaa   22740
atcagatccg cgtccaggtc ctcgcgttg tcaggcga acggagtcaa ctttggtagc      22800
tgccttccca aaagggcgc gtgcccaggc tttgagttgc actcgcaccg tagtggcatc   22860
aaaaggtgac cgtgccaggt ctgggcgtta ggatacgacg cctgcataaa agccttgatc   22920
tgcttaaaag ccacctgagc cttttgcgcct tcagagaaga acatgccgca agacttgccg   22980
gaaaactgat tggccggaca ggccgcgtcg tgcacgcagc accttgcgtc ggtgttggag   23040
atctgcacca catttcggcc ccaccggttc ttcacgatct tggccttgct agactgctcc   23100
ttcagcgcgc gctgcccgtt ttcgctcgtc acatccattt caatcacgtg ctccttattt   23160
atcataatgc ttccgtgtag acacttaagc tcgccttcga tctcagcgca gcggtgcagc   23220
cacaacgcgc agcccgtggg ctcgtgatgc ttgtaggtca cctctgcaaa cgactgcagg   23280
tacgcctgca ggaatcgccc catcatcgtc acaaggtct tgttgctggt gaaggtcagc    23340
tgcaacccgc ggtgctcctc gttcagccag gtcttgcata cggccgccag agcttccact   23400
tggtcaggca gtagtttgaa gttcgccttt agatcgttac ccacgttgtc ccacgtcatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
cttcttcct cgctgtccac gattacctcc ggtgatgcg ggcgctcggg cttgggagaa     23760
gggcgcttct tttcttctt gggcgcaatg gccaaatccg ccgccgaggt cgatggccgc    23820
gggcgtgggt tgcgcggcac cagcgcgtct tgtgatgagt cttcctcgtc ctcggactcg   23880
atacgccgcc tcatccgctt ttttgggggc gcccggggag gcggcggcga cgggacggg    23940
gacgacacgt cctccatggt tggggacgt cgcgccgcac cgcgtccgcg ctcggggtg      24000
gtttcgccgt gctcctcttc ccgactggcc atttcctct cctataggca gaaaagatc     24060
atggagtcag tcgagaagaa ggacagccta accgcccct ctgagttcgc caccaccgcc    24120
tccaccgatg ccgccaacgc gcctaccacc ttccccgtcg aggcaccccc gcttgaggag   24180
gaggaagtga ttatcgagca ggacccaggt tttgtaagcg aagacgacga ggaccgctca   24240
gtaccaacag aggataaaaa gcaagaccag gacaacgcag aggcaaacga ggaacaagtc   24300
gggcgggggg acgaaaggca tggcgactac ctagatgtgg gagacgacgt gctgttgaag   24360
```

```
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccaccttat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc tcaaggtcat gagcacagtc  24900
atgagtgagc tgatcgtgcg ccgtgccgca cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac cctgcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gacttgtgc ccattaagta ccgcgaatgc cctccgccgc tttgggccca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct tgagctgcaa gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg accccccagtc cggcgaggag ctcaaccccaa tcccccgcc gcgcagcccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttccctctcg cggcgcccca  26400
gaaatcggca accggttcca gcatggctac aacctccgct cctcaggcgc cgccggcact  26460
gcccgttcgc cgacccaacc gtagatggga caccactgga accagggccg gtaagtccaa  26520
gcagccgccg ccgttagccc aagagcaaca acagcgccaa ggctaccgct catgcgcgg  26580
gcacaagaac gccatagttg cttgcttgca agactgtggg ggcaacatct ccttcgcccg  26640
ccgcttttctt ctctaccatc acggcgtggc cttccccgt aactcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tcccagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgccgatccc caccccgcagc tgcctgtatc  27000
acaaaagcga agatcagctt cggcgcacgc tggaagacgc ggaggctctc ttcagtaaat  27060
actgcgcgct gactcttaag gactagttc gcgcccttc tcaaatttaa gcgcgaaaac  27120
tacgtcatct ccagcggcca cacccgcgc cagcacctgt cgtcagcgca attatgagca  27180
aggaaattcc cacgccctac atgtggagtt accagccaca aatgggactt gcggctggaa  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataaacctt aatccccgta gttggccctgc tgcctggtta taccaggaaa  27420
gtcccgctcc caccactgtg gtacttccca gagacgccca ggccgaagtt cagatgacta  27480
actcaggggc gcagcttgcg gcggcttttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacattc agatcggcgg cggccgt cctttcattca  27660
cgcctcgtca ggcaatccta actctgcaga cctcgtcctc tgagccgcgc tctggaggca  27720
ttggaactct gcaattattt gaggagttg tgccatcggt ctactttaac cccttctcgg  27780
gacctccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acgcgtccg gcttaccgcc cagggagagc  28020
ttgcccgtag cctgattcgg gagtttaccc agcgccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtacttta acatctctcc ctctgtgatt tacaacagtt caacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagacttt tccggacaga cctcaataac tctgttttacc agaacaggag gtgagcttag  28500
aaaaccctta gggtattagg ccaaaggcgc agctactgtg gggttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acgtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatacttttc cattttatga aatgtgcgac  29040
attaccatgt acatgagcaa acagtataag ttgtggcccc cacaaaattg tgtggaaaac  29100
```

```
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca acctttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
accggactta catctaccac aaatacaccc caagttctg cctttgtcaa taactgggat  29580
aacttgggca tgtggtggtt ctccatagcg ctttatgttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg accccttgttg  29820
cgcttttttg tgcgtgctcc acattggctg cggtttctca catcgaagta gactgcattc  29880
cagccttcac agtctatttg cttttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc ccccaacttt ccccgcgccc gctatgcttc cactgcaaca  30360
agttgttgcc ggcggctttg tcccagccaa tcagcctcgc cccactctc ccaccccac  30420
tgaaatcagc tactttaatc taacaggagg agatgactga caccctagat ctagaaatgt  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctccctt  31140
gtatccccca atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaaccacc tcaccatgca atcacagcc  31440
ccgctaaccg tgcacgactc caaacttagc attgccaccc aaggacccct cacagtgtca  31500
gaaggaaagc tagccctgca aacatcaggc ccctcacca ccaccgatag cagtaccctt  31560
actatcactg cctcaccccc tctaactact gccactggta gcttgggcat tgacttgaaa  31620
gagccattt atacacaaaa tggaaaacta ggactaaagt acgggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aatttggcat ggcctagaat ttgattcaaa caaggctatg  32160
gttcctaaac taggaactgg ccttagtttt gacagcacag gtgccattac agtaggaaac  32220
aaaaaataatg ataagctaac tttgtggacc acaccagctc catctcctaa ctgtagacta  32280
aatgcagaga aagatgctaa actcacttg gtcttaacaa aatgtggcag tcaaatactt  32340
gctacagttt cagttttggc tgttaaaggc agtttggcc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
acttttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga atctaatagt tcaacctgcc  32940
acctccctcc caacacacag agtacacagt ccttttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctactgg gggtagagtc ataatcggt atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtgcgac tttcataaa  33540
cacgctggac ataaacatta cctcttttgg catgttgtaa ttcaccacct cccggtacca  33600
tataaacctc tgattaaaca tggcgccatc caccaccatc ctaaaccagc tggcaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
```

```
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacgagt gcgccgaga    34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acgggaggag   34320
cgggaagagc tggaagaacc atgttttttt tttattcca aaagattatc caaaacctca    34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
ccagcacctt caaccatgcc caaataattc tcatctcgcc accttctcaa tatatctcta   34620
agcaaatccc gaatattaag tccggccatt gtaaaaatct gctccagagc gccctccacc   34680
ttcagcctca agcagcgaat catgattgca aaaattcagg ttcctcacag acctgtataa   34740
gattcaaaag cggaacatta acaaaaatac cgcgatcccg taggtccctt cgcagggcca   34800
gctgaacata atcgtgcagg tctgcacgga ccagcgcggc cacttccccg ccaggaacca   34860
tgacaaaaga acccacactg attatgacac gcatactcgg agctatgcta accagcgtag   34920
ccccgatgta agcttgttgc atgggcggcg atataaaatg caaggtgctg ctcaaaaaat   34980
caggcaaagc ctcgcgcaaa aaagaaagca catcgtagtc atgctcatgc agataaaggc   35040
aggtaagctc cggaaccacc acagaaaaag acaccatttt tctctcaaac atgtctgcgg   35100
gtttctgcat aaacacaaaa taaaataaca aaaaaacatt taaacattag aagcctgtct   35160
tacaacagga aaaacaaccc ttataagcat aagacggact acggccatgc cggcgtgacc   35220
gtaaaaaaac tggtcaccgt gattaaaaag caccaccgac agtcctcgg tcatgtccgg     35280
agtcataatg taagactcgg taaacacatc aggttgattc acatcggtca gtgctaaaaa   35340
gcgaccgaaa tagcccgggg gaatacatac ccgcaggcgt agacaacaa ttacagccgg     35400
cataggaggt ataacaaaat taataggaga gaaaaacaca taaacacctg aaaaaccctc   35460
ctgcctaggc aaaatagcac cctcccgctc cagaacaaca tacagcgctt ccacagcggc   35520
agccataaca gtcagcctta ccagtaaaaa agaaaaccta ttaaaaaaac caccatcgac   35580
acggcaccag ctcaatcagt cacagtgtaa aaaagggcga agtgcagagc gagtatatat   35640
aggactaaaa aatgacgtaa cggttaaagt ccacaaaaaa cacccagaaa accgcacgcg   35700
aacctacgcc cagaaacgaa agccaaaaaa cccacaactt cctcaaatcg tcacttccgt   35760
tttcccacgt tacgtaactt cccatttttaa gaaaactaca attccaaca catacaagtt   35820
actccgcccct aaaacctacg tcacccgccc cgttccacg ccccgcgcca cgtcacaaac    35880
tccacccccct cattatcata ttggcttcaa tccaaaataa ggtatattat tgatgatg     35938

SEQ ID NO: 2           moltype = DNA   length = 10
FEATURE                Location/Qualifiers
misc_feature           1..10
                       note = Sequence resulting from TAV-255 deletion
source                 1..10
                       mol_type = other DNA
                       organism = synthetic construct
SEQUENCE: 2
ggtgttttgg                                                               10

SEQ ID NO: 3           moltype =    length =
SEQUENCE: 3
000

SEQ ID NO: 4           moltype =    length =
SEQUENCE: 4
000

SEQ ID NO: 5           moltype =    length =
SEQUENCE: 5
000

SEQ ID NO: 6           moltype = DNA   length = 46
FEATURE                Location/Qualifiers
misc_feature           1..46
                       note = Exempalry modified E1b-19k region
source                 1..46
                       mol_type = other DNA
                       organism = synthetic construct
SEQUENCE: 6
atcttggtta catctgacct cgtcgagtca ccaggcgctt ttccaa                       46

SEQ ID NO: 7           moltype = DNA   length = 1185
FEATURE                Location/Qualifiers
misc_feature           1..1185
                       note = mTGFB-Trap
source                 1..1185
                       mol_type = other DNA
                       organism = synthetic construct
SEQUENCE: 7
atgggtcggg ggctgctccg gggcctgtgg ccgctgcata tcgtcctgtg acgcgcatc         60
gccagcacga tcccgccgca cgttcccaag tcggttaaca gtgatgtcat ggccagcgac       120
aatggcggtg cggtcaagct tccacagctg tgcaagtttt gcgatgtgag actgtccact       180
```

```
tgcgacaacc agaagtcctg catgagcaac tgcagcatca cggccatctg tgagaagccg    240
catgaagtct gcgtggccgt gtggaggaag aacgacaaga acattactct ggagacggtt    300
tgccacgacc ccaagctcac ctaccacggc ttcactctgg aagatgccgc ttctcccaag    360
tgtgtcatga aggaaaagaa aagggcgggc gagactttct tcatgtgtgc ctgtaacatg    420
gaagagtgca acgattacat catcttttcg gaagaatcaa ccaccagcag tcccgacagc    480
accaaggtgg acaagaaaat tgtgcccagg gattgtggtt gtaagccttg catatgtaca    540
gtcccagaag tatcatctgt cttcatcttc cccccaaagc ccaaggatgt gctcaccatt    600
actctgactc ctaaggtcac gtgtgttgtg gtagacatca gcaaggatga tcccgaggtc    660
cagttcagct ggtttgtaga tgatgtggag gtgcacacag ctcagacgca accccgggag    720
gagcagttca acagcacttt ccgctcagtc agtgaacttc ccatcatgca ccaggactgg    780
ctcaatggca aggagttcaa atgcagggtc aacagtgcag cttcccctgc ccccatcgag    840
aaaaccatct ccaaaaccaa aggcagaccg aaggctccgc aggtgtacac cattccacct    900
cccaaggagc agatggccaa ggataaagtc agtctgacct gcatgataac agacttcttc    960
cctgaagaca ttactgtgga gtggcagtgg aatgggcagc cagcggagaa ctacaagaac   1020
actcagccca tcatggacac agatggctct tacttcgtct acagcaagct caatgtgcag   1080
aagagcaact gggaggcagg aaatactttc acctgctctg tgttacatga gggcctgcac   1140
aaccaccata ctgagaagag cctctcccac tctcctggta aatga                   1185

SEQ ID NO: 8            moltype =    length =
SEQUENCE: 8
000

SEQ ID NO: 9            moltype =    length =
SEQUENCE: 9
000

SEQ ID NO: 10           moltype = DNA  length = 10
FEATURE                 Location/Qualifiers
misc_feature            1..10
                        note = Sequence resulting from exemplary E1A promoter CAAT
                         box deletion
source                  1..10
                        mol_type = other DNA
                        organism = synthetic construct
SEQUENCE: 10
ttccgtggcg                                                             10

SEQ ID NO: 11           moltype =    length =
SEQUENCE: 11
000

SEQ ID NO: 12           moltype = DNA  length = 10
FEATURE                 Location/Qualifiers
source                  1..10
                        mol_type = unassigned DNA
                        organism = Adenovirus type 5
SEQUENCE: 12
taataaaaaa                                                             10

SEQ ID NO: 13           moltype =    length =
SEQUENCE: 13
000

SEQ ID NO: 14           moltype = DNA  length = 11
FEATURE                 Location/Qualifiers
source                  1..11
                        mol_type = unassigned DNA
                        organism = Adenovirus type 5
SEQUENCE: 14
taaaaaaaaa t                                                           11
```